United States Patent [19]

Nakamura et al.

[11] 4,304,847
[45] Dec. 8, 1981

[54] COLOR IMAGE FORMING DYE BLEACH PROCESS

[75] Inventors: Koichi Nakamura; Isao Shimamura; Yukio Maekawa; Koichi Koyama; Shigeki Yokoyama, all of Minami-ashigara, Japan

[73] Assignee: Fuji Photo Film Co., Ltd., Minami-ashigara, Japan

[21] Appl. No.: 93,489

[22] Filed: Nov. 13, 1979

[30] Foreign Application Priority Data

Nov. 13, 1978 [JP] Japan .................. 53/139582

[51] Int. Cl.³ .................................. G03C 7/00
[52] U.S. Cl. ........................ 430/390; 430/353; 430/391; 430/392; 430/460; 430/462; 430/455
[58] Field of Search ............. 430/390, 391, 392, 429, 430/462, 455, 460

[56] References Cited

U.S. PATENT DOCUMENTS

| | | | |
|---|---|---|---|
| 1,517,049 | 11/1924 | Christensen | 430/390 |
| 2,184,022 | 12/1939 | Seymour | 430/390 |
| 2,311,015 | 2/1943 | Young et al. | 430/390 |
| 2,322,001 | 6/1943 | Ehrenfried | 430/390 |
| 2,326,055 | 8/1943 | Morris | 430/390 |
| 2,350,736 | 6/1944 | Ehrenfried | 430/390 |
| 3,414,411 | 12/1968 | Michel et al. | 430/390 |
| 3,658,535 | 4/1972 | Willems | 430/391 |
| 3,870,519 | 3/1975 | Pillar | 430/390 |
| 4,186,008 | 1/1980 | Schar et al. | 430/462 |

Primary Examiner—Travis Brown
Attorney, Agent, or Firm—Sughrue, Rothwell, Mion, Zinn & Macpeak

[57] ABSTRACT

A color image forming process which comprises processing a photographic light-sensitive element comprising a support having thereon a layer containing imagewise distributed silver therein with an aqueous alkaline solution containing a stannous ion and in the presence of a dye and a bispyridinium compound represented by the following general formula:

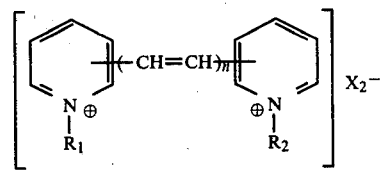

wherein $R_1$ and $R_2$ each represents a lower aliphatic hydrocarbon group or $R_1$ and $R_2$ are bonded each other to form a ring; n represents 0 or 1; and $X^-$ represents an anion; to bleach the dye in an imagewise manner. By the process of the present invention, color images which are stable to light, heat and moisture are formed using light-sensitive elements containing a reduced amount of silver salt and without using chemicals causing environmental pollution problems for the processing.

39 Claims, No Drawings

COLOR IMAGE FORMING DYE BLEACH PROCESS

BACKGROUND OF THE INVENTION

1. Field of the Invention

The present invention relates to a color image forming process. More particularly, the present invention relates to a color image forming process which comprises processing a photographic element comprising a support having thereon a layer containing imagewise distributed silver with an aqueous alkaline solution containing a stannous ion in the presence of a dye to bleach the dye in an imagewise manner.

2. Description of the Prior Art

In a general process of forming color images, azomethine dyes or indoaniline dyes are formed by developing silver halide light-sensitive materials in the presence of couplers using a primary aromatic amine developing agent. Color development using silver halide is based on the process invented by L. D. Nannes and L. Godowsky in 1935. Various improvements have been made in the process since and in general the system has been employed worldwide in the photographic art.

Color development using a primary aromatic amine developing agent generally has the following disadvantages. (1) The dyes formed by the system have poor light resistance, heat resistance, and moisture resistance and, hence, the color images formed have a great tendency to fade with the passage of time, (2) a primary aromatic amine developing agent is toxic, for example, causing skin rashes and, thus, specific precautions are required in using this type of developing agent, and (3) since there is an equivalency relationship between the dye image and the oxidation product of the color developing agent, it is theoretically difficult to reduce the amount of the silver halide which takes part in the dye formation to an amount lower than the stoichiometrically required amount.

Conventional techniques for reducing the amount of silver halide in color photography can be classified into reducing the amount of silver halide to as low as level as possible and reducing the stoichiometrically required amount of the silver halide itself. In regard to the latter approach, the so-called two equivalent couplers capable of forming one molecule of dye with two molecules of silver halide have been developed. However, even using this technique, it is theoretically difficult to reduce the amount of silver salt in the light-sensitive materials to less than ½ of the amount of silver salt in light-sensitive materials containing couplers other than two equivalent couplers.

Another color photographic process presently employed is the silver-dye-bleach photographic process. This process is based on the color photographic process invented by Gaspar and, since azo dyes are used in the color process, the color images formed by the process generally have excellent light resistance, heat resistance and moisture resistance. A typical photographic element used for the silver-dye-bleach color photographic process has three silver halide photographic emulsion layers respectively sensitized to red, green and blue light, and having associated therewith, respectively, a bleachable cyan, magenta and yellow dye. Such a photographic element provides color photographic positive images through the following processing.

(1) The photographic element is imagewise exposed.

(2) The exposed photographic element is developed in a silver halide developer to form negative silver images.

(3) The photographic element is then processed in a dye bleach bath which oxidizes the silver images to a silver salt and concurrently decolorizes the associated dye pattern, and (4) Finally the photographic element is fixed and washed to remove the residual silver salt, whereby dye images are obtained which are photographically the reverse of the initial silver images. The silver-dye-bleach process is generally described in, for example, U.S. Pat. Nos. 3,498,787 and 3,503,741, Canadian Pat. No. 790,533 and A. Meyer, "Some Features of the Silver-Dye-Bleach Process", *The Journal of Photographic Science*, Vol. 13, pp. 90–97 (1965).

In the silver-dye-bleach process described in U.S. Pat. No. 2,270,118, dye images are formed by processing dye-containing layers having silver images therein with an acid solution which decomposes the dyes in the areas where silver is present. The decomposition or destruction of the dye is accelerated by various "catalysts" such as phenazine. Also, the reaction in these dye bleach systems is believed to proceed on a stoichiometric basis (for example, U.S. Pat. No. 3,340,060 in Column 1, lines 18–21 suggests that 4 atoms of silver are required for decomposing one azo dye group). However, these silver-dye-bleach processes have the following disadvantages:

(1) Since a large amount of silver is required for bleaching the dyes, the photosensitive materials must contain a large amount of silver halide in the silver halide photographic emulsion layers.

(2) Since a strongly acidic processing solution, which is highly corrosive, is usually used in these processes, difficulties are encountered in maintenance of the processing apparatus and handling the processing solution.

Also, another silver-dye-bleach process is described in U.S. Pat. Nos. 1,517,049 and 2,184,022. According to the method dyes are decomposed imagewise using sodium hydrosulfite or stannous chloride as a reducing agent. In the process, however, the decomposition rate of the dye is extremely small and thus a long bleaching time is required as shown in Examples 1 and 2 below. In order to carry out processing in a short period of time, it is necessary to use a vat dye such as indigo which is easily decomposed. Therefore, dyes suitable for a photographic system cannot be freely used which is a disadvantage of the method.

SUMMARY OF THE INVENTION

An object of the present invention, therefore, is to provide a process of forming color photographic images using light-sensitive materials containing a reduced amount of silver salt compared with conventional color light-sensitive materials.

Another object of the present invention is to provide a process of forming color photographic images having excellent light resistance, heat resistance and moisture resistance.

Still another object of the present invention is to provide a process of forming color photographic images using a less corrosive processing solution without exhausting harmful substances in waste water.

These objects of the present invention are accomplished by processing a photographic element containing imagewise distributed silver with an aqueous alkaline solution containing a stannous ion and in the presence of a dye and a bispyridinium compound represented by the formula (I):

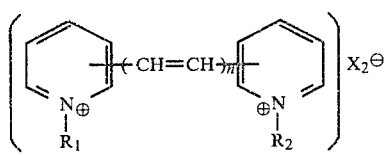

wherein $R_1$ and $R_2$ each represents a lower aliphatic hydrocarbon group or $R_1$ and $R_2$ are bonded to each other to form a ring; n represents 0 or 1; and $X^\ominus$ represents an anion; to bleach the dye in an imagewise manner.

DETAILED DESCRIPTION OF THE INVENTION

According to the process of the present invention, imagewise distributed silver in the photographic element plays the role of a catalyst and hence the amount of silver salt employed in the photographic element can be greatly reduced. That is, in the process of the present invention, the bleaching of the dye can be sufficiently performed with about one-fifth the amount of silver required in the conventional silver-dye-bleach process.

The process of the present invention relies upon an imagewise distribution of silver. The silver pattern, however, need not be obtained by exposure and development of a conventional silver halide emulsion. In still another embodiment of the present invention, a print-out silver image formed by imagewise exposing a silver salt photographic material is utilized. Such a photographic element contains a known halogen-acceptor for accelerating the print-out effect or a silver salt capable of being easily thermally decomposed, such as a silver salt of a fatty acid. In the process of the present invention, a print-out silver image is formed by exposing a photographic element containing such a silver salt and a dye and then the imagewise exposed photographic element is immersed in an aqueous alkaline solution containing a stannous salt and a bispyridinium compound, whereby the dye is bleached at the areas containing the print-out silver image to provide a color positive image.

The present invention can also be applied to a photographic element in which a silver image pattern is formed upon heat development, that is, in the process, an element containing a light-sensitive silver salt, a reducing agent, a silver providing agent such as silver behenate and a dye is imagewise exposed and then heated, whereby a silver image is formed. The silver image formed acts as a catalyst to bleach the dye.

In a particularly preferred embodiment of the present invention, color positive images are obtained by imagewise exposing a photograpic element having at least one layer containing silver halide emulsion and a dye followed by development to form an image pattern of developed silver, removing the remaining silver halide using a fixing solution containing a thiosulfate and a bispyridinium compound and then processing the photographic element in an aqueous alkaline solution containing a stannous salt and an organic phosphonic acid to bleach the dye at the areas containing the developed silver.

In another embodiment of the present invention, color negative images are obtained using a direct positive silver halide emulsion as the silver halide emulsion in the above-described embodiments.

In still another embodiment of the present invention, color positive images are obtained by imagewise exposing a photographic element having at least one silver halide emulsion layer followed by development, then immersing the photographic element in a bath containing a dye and a bispyridinium compound to dye the photographic element with the dye, and then immersing the dyed photographic element in an alkaline aqueous solution containing a stannous salt to bleach the dye in an imagewise manner.

A conventional photographic material contains about 3 to about 10 $g/m^2$ of silver salt as silver and a photographic print material contains about 1 to about 4 $g/m^2$ of silver. The coated amount of silver in the photographic material used in the present invention is less than about 3 $g/m^2$, in particular, less than 2 $g/m^2$. Also, in the case of a multilayer photographic material used in the present invention, the coated amount of silver for each silver halide emulsion layer is less than about 1 $g/m^2$, in particular, about 10 $mg/m^2$ to 0.5 $g/m^2$.

According to one embodiment of the present invention, color images are formed by processing a photographic element containing imagewise distributed silver with an aqueous alkaline solution containing a stannous salt in the presence of a dye and a bispyridinium compound to bleach the dye in an imagewise manner.

In a preferred embodiment of the present invention, color positive images are obtained by imagewise exposing a photographic element having at least one layer containing silver halide emulsion and a dye followed by development to form an image pattern of developed silver, removing the remaining silver halide using a fixing solution containing a thiosulfate and a bispyridinium compound and then processing the photographic element in an aqueous alkaline solution containing a stannous salt to bleach the dye in the areas containing the developed silver.

Although the principle of the process of the present invention is not at present clear and while not desiring to be bound, it is believed that silver present in the photographic element acts as a catalyst for decomposing the stannous salt to a stannic salt and concurrently the bispyridinium compound is converted to its reduced form and the reduced bispyridinium compound reductively decomposes the dye.

In a conventional silver-dye-bleach process, a catalyst such as phenazine reacts with imagewise distributed silver to form the reduction product (dihydro compound) of phenazine which reductively bleaches the dye, and thus the dye is decomposed via a leuco material. With an azo dye which is usually used, 4 equivalents of silver are required for decomposing each azo group equivalent. On the other hand, surprisingly in the process of the present invention, only ½ to ⅓ equivalent of silver is usually required for decomposing one azo group equivalent of a dye. While on superficial examination, the present invention might seem similar to a conventional silver-dye-bleach process since the dye is reductively decomposed, however, in the present invention, silver is believed to act as a catalyst to decompose the stannous salt to the stannic salt, while silver per se acts as a reducing agent in a conventional silver-dye-bleach process. As a result, there is marked difference between the process of the present invention and the above-described conventional silver-dye-bleach process in terms of the quantitative relationship between silver and dye. In the photographic elements which may be employed in the present invention, the dye is incorporated into the photographic material in an amount of at least about 100% excess, preferably at least 200% excess, over the stoichiometrically required amount based on the silver salt employed.

Practically any stannous salts, inorganic, organic or chelated can be used in the present invention since these salts finally take the form of $SnO_2^{2-}$ in a process solution. The stannous salt which can be used in the present invention includes, for example, $SnCl_2$, $SnSO_4$, $Sn(NO_3)_2$, $Sn(CH_3COO)_2$, $SnC_2O_4$, etc.

The bispyridinium compounds suitable for use in the present invention are represented by the formula (I):

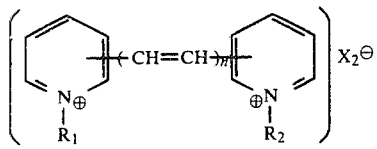

wherein $R_1$ and $R_2$ each represents a lower aliphatic hydrocarbon group or $R_1$ and $R_2$ are bonded to each other to form a ring; n represents 0 or 1; and $X^\ominus$ represents an anion. $R_1$ and $R_2$ are preferably lower alkyl groups, e.g., having 1 to 4 carbon atoms or combine to form a polymethylene chain which may include a lower alkyl substituent. $X^\ominus$ in the formula is an anion such as a halogen (F, Cl, Br) ion, $HNO_3^\ominus$, or an anion of an aliphatic or aromatic carboxylic or sulfonic acid.

As a more preferred embodiment of the invention the bispyridinium compound is of the formula (Ia) or (Ib):

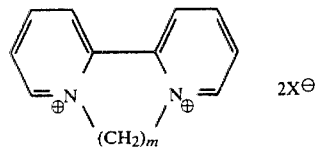
(Ia)

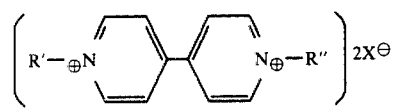
(Ib)

wherein m represents an integer of 2 to 4; R' and R" each represents an alkyl group having 1 to 3 carbon atoms; and $X^\ominus$ represents an anion.

Specific examples of the bispyridinium compounds which can be used in the present invention are shown below:

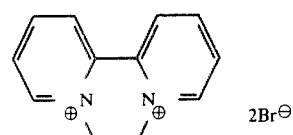
Compound 1

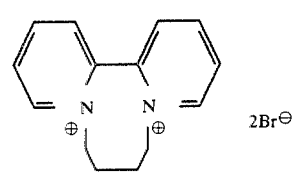
Compound 2

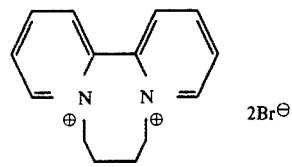
Compound 3

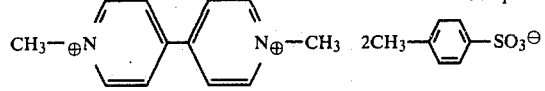
Compound 4

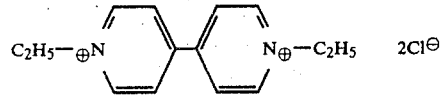
Compound 5

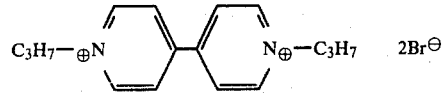
Compound 6

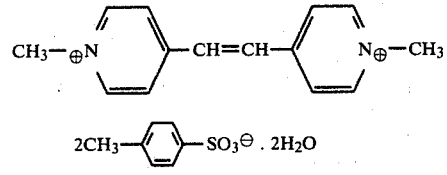
Compound 7

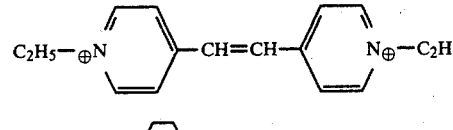
Compound 8

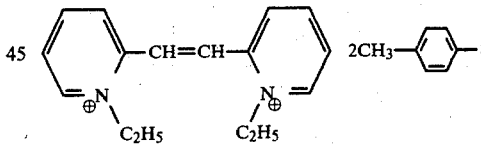
Compound 9

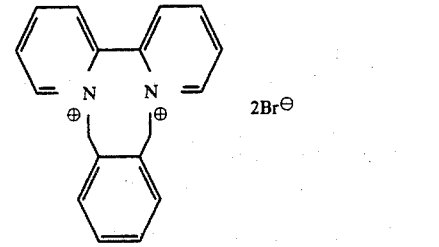
Compound 10

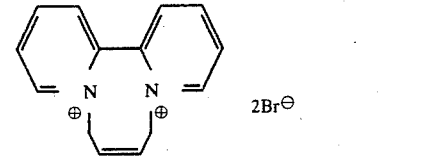
Compound 11

Compound 12

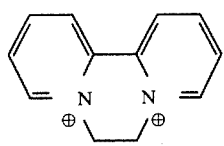

Compound 3 above is particularly preferred.

Compounds 1 to 9 and 12 described above are all known compounds and can be synthesized by the methods described in, for example, L. A. Summer, *Tetrahedron*, Vol. 24, page 2697 (1968), ibid., Vol. 24, page 5433 (1968), ibid., Vol. 24, page 6453 (1968), *J. Heterocyclic Chem.*, Vol. 7, page 719 (1970), ibid., Vol. 7, page 401 (1970), ibid., Vol. 8, page 29 (1971), *J. Chem. Soc.*, (C), 1643 (1969), etc. Compound 11 described above is described in *J. Chem. Soc.*, 5816 (1965).

Compound 10 and Compound 11 described above can be synthesized in the manner described in the following Synthesis Examples.

SYNTHESIS EXAMPLE 1

Synthesis of Compound 10

7 g of α,α'-dipyridyl and 25 g of orthoxylene bromide were added to 50 ml of dimethylformamide. The mixture was refluxed under heating in an oil bath for 3 hours. After cooling the mixture, the crystals formed were collected by filtration and recrystallized from ethanol to obtain 14 g of needle crystals having a melting point of above 350° C.

Elemental Analysis for $C_{18}H_{16}N_2Br_2$: Calcd. (%): C: 51.43 H: 3.81 N: 6.67; Found (%): C: 51.38 H: 3.87 N: 6.95.

SYNTHESIS EXAMPLE 2

Synthesis of Compound 11:

8 g of Compound 1 was dissolved in 100 ml of water and the solution was stirred at room temperature. To the solution, 100 ml of a solution containing 7 g of silver nitrate dissolved in water was gradually added dropwise. After the completion of the addition, the silver bromide formed was removed by filtration and the filtrate was concentrated under reduced pressure. The crystals formed were recrystallized from ethanol to obtain 4 g of colorless needle crystals having a decomposition point of 215° C.

Elemental Analysis for $C_{12}H_{12}N_4O_6$: Calcd. (%): C: 46.76 H: 3.92 N: 18.18; Found (%): C: 46.54 H: 3.90 N: 17.90.

The bispyridinium compound can be added to a developer solution, a fixing solution, a dye bleach solution and/or other bath between a development step and a dye bleach step.

The dye bleach solution containing a stannous salt preferably contains an organic phosphonic acid or a salt thereof. The organic phosphonic acid or the salt thereof is a compound having at least one phosphonic acid group in its molecule. Preferred phosphonic acids or salts thereof are represented by the following general formulae (II), (III) and (IV):

$$R_3N(CH_2PO_3M_2)_2 \quad (II)$$

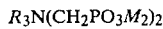

wherein M represents a hydrogen atom or a cation capable of rendering the compound water soluble (for example, an alkali metal such as sodium, potassium, etc., ammonium, pyridinium, triethanolammonium, trie-thylammonium ion, etc.); and $R_3$ represents an alkyl group having 1 to 4 carbon atoms (for example, methyl, ethyl, propyl, isopropyl, butyl group, etc.), an aryl group having 6 to 8 carbon atoms (for example, phenyl, o-tolyl, m-tolyl, p-tolyl, p-carboxyphenyl, a water-soluble salt of a p-carboxyphenyl group (for example, a sodium, potassium salt, etc.), etc.), an aralkyl group (for example, a benzyl group, a β-phenethyl group, an o-acetamidobenzyl group, etc., and preferably an aralkyl group having 7 to 9 carbon atoms), a saturated or unsaturated alicyclic group having 5 to 8 carbon atoms (for example, cyclohexyl, cyclopentyl group, etc.), or a saturated or unsaturated heterocyclic residue containing one or more nitrogen, sulfur or oxygen atoms. The heterocyclic ring may be a 5-or 6-membered ring and may be condensed with a 5- to 7-membered carbocyclic ring (for example, pyrrolidylmethyl, pyrrolidylbutyl, benzothiazolylmethyl, tetrahydroquinolylmethyl group, etc.). The group represented by $R_3$, particularly the alkyl group, may be substituted with a hydroxy group, an alkoxy group (for example, a methoxy group, an ethoxy group, etc.), a halogen atom (for example, a chlorine atom, etc.), $-PO_3M_2$, $-CH_2PO_3M_2$ or $-N(CH_2PO_3M_2)_2$ (wherein M has the same meaning as defined above), etc.

$$R_4R_5C(PO_3M_2)_2 \quad (III)$$

wherein $R_4$ represents a hydrogen atom, a $C_1$–$C_4$ alkyl group, a monocyclic aralkyl group having 6 to 8 carbon atoms, a saturated or unsaturated alicyclic group having 1 to 4 carbon atoms, a 5- or 6-membered heterocyclic residue as defined above for $R_3$, $-CHR_6-PO_3M_2$ (wherein $R_6$ represents a hydrogen atom, a hydroxy group or a $C_1$–$C_4$ alkyl group) or $-PO_3M_2$; and $R_5$ represents a hydrogen atom, a hydroxy group, an alkyl group, a substituted alkyl group as defined above for $R_3$ or $-PO_3M_2$ (wherein M has the same meaning as defined above).

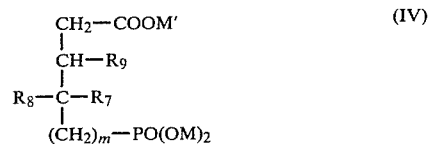

wherein $R_7$ represents $-COOM'$ or $-PO(OM)_2$; $R_8$ represents a hydrogen atom, an alkyl group having 1 to 4 carbon atoms, $-(CH_2)_nCOOM'$ or a phenyl group; $R_9$ represents a hydrogen atom or $-COOM'$; M and M' each represents a hydrogen atom, an alkali metal atom or an ammonium group; m is 0 or 1; and n represents 1 to 4. In the above formula (IV), $R_8$ represents preferably a hydrogen atom, a methyl group or a carboxymethyl group.

Representative examples of the compounds represented by the general formula (II) are illustrated below:

1. Ethylenediamine-N,N,N',N'-tetramethylenephosphonic acid
2. Nitrilo-N,N,N-trimethylenephosphonic acid
3. 1,2-Cyclohexanediamine-N,N,N',N'-tetramethylenephosphonic acid
4. o-Carboxyaniline-N,N-dimethylenephosphonic acid
5. Propylamine-N,N-dimethylenephosphonic acid 6. 4-(N-Picolidino)butylamine-N,N-bis(methylenephosphonic acid)

7. 1,3-Diaminopropanol-N,N,N',N'-tetramethylenephosphonic acid 8. 1,3-Propanediamine-N,N,N',N'-tetramethylenephosphonic acid 9. 1,6-Hexanediamine-N,N,N',N'-tetramethylenephosphonic acid 10. o-Acetamidobenzylamine-N,N-dimethylenephosphonic acid 11. o-Toluidine-N,N-dimethylenephosphonic acid 12. 2-Pyridylamine-N,N-dimethylenephosphonic acid Representative examples of the compounds represented by the general formula (III) are illustrated below:

13. 1-Hydroxyethane-1,1-diphosphonic acid
14. Ethane-1,1,1-triphosphonic acid
15. 1-Hydroxy-2-phenylethane-1,1-diphosphonic acid
16. 2-Hydroxyethane-1,1-diphosphonic acid
17. 1-Hydroxyethane-1,1,2-triphosphonic acid
18. 2-Hydroxyethane-1,1,2-triphosphonic acid
19. Ethane-1,1-diphosphonic acid
20. Ethane-1,2-diphosphonic acid Representative examples of the compounds represented by the general formula (IV) are illustrated below:

21. 1-Phosphonopropane-1,2,3-tricarboxylic acid
22. 1-Phosphonobutane-2,3,4-tricarboxylic acid
23. 1,1-Diphosphonopropane-2,3-dicarboxylic acid
24. 2-Phosphonobutane-2,3,4-tricarboxylic acid
25. 2,2-Diphosphonobutane-3,4-dicarboxylic acid
26. 2-Phosphonobutane-1,2,4-tricarboxylic acid Of the above acids, 2-hydroxyethane-1,1-diphosphonic acid, 1-hydroxyethane-1,1-diphosphonic acid, ethane-1,1,1-triphosphonic acid, 1-hydroxyethane-1,1,2-triphosphonic acid or 2-phosphonobutane-1,2,4-tricarboxylic acid are preferred.

The dyes used in the present invention are reductively bleachable dyes and illustrative examples include azo dyes, anthraquinone dyes, etc. Azo dyes are more preferred. Typical examples of these dyes are described in Color Index, Vol. 4, 3rd Edition, The Society of Dyers and Colorists. Particularly suitable dyes which can be used in this invention are azo dyes such as monoazo dyes (C.I. 11,000–19,999); bisazo dyes (C.I. 20,000–29,999); triazo dyes (C.I. 30,000–34,999); polyazo dyes (C.I. 35,000–36,999); triarylmethane dyes (C.I. 42,000–44,999); acridine dyes (C.I. 46,000–46,999); azine dyes (C.I. 50,000–50,999); thiazine dyes (C.I. 52,000–52,999); anthraquinone dyes (C.I. 58,000–72,999). (In the descriptions given herein "C.I" designates the Color Index number.)

Also, dyes conventionally used in a silver-dye-bleach process can be used in the process of the present invention.

Yellow dyes used usually include azo dyes such as Direct Fast Yellow GC (C.I. 29,000), Sirius Supra Yellow R (C.I. 29,025), Chrysophenine (C.I. 24,985), etc.; benzoquinone dyes, anthraquinone dyes and polycyclic soluble vat dyeing dyes such as Indigosol Yellow HCGN (C.I. 56,006), Indigosol Golden Yellow IGK (C.I. 59,101), Indigosol Yellow 2 GB (C.I. 61,726), Algosol Yellow GCA-CF (C.I. 67,301), Indigosol Yellow V (C.I. 60,531), Indanthrene Yellow 4 GF (C.I. 68,420), Indanthrene Yellow G (C.I. 70,600), Mikethren Yellow GC (C.I. 67,300), Indanthrene Yellow 4 GK (C.I. 68,405), etc. Also, magenta dyes generally used include azo dyes such as Nippon Fast Red BB (C.I. 29,100), Sirius Supra Rubbine B (C.I. 25,380), Sumilight Supra Rubinol B (C.I. 29,225), Benzo Brilliant Gelanine B (C.I. 15,080), etc.; soluble vat dyes selected from indigoid series, benzoquinone series and anthraquinone series heteropolycyclic compounds such as Indigosol Brilliant Pink IR (C.I. 73,361), Indigosol Red Violet IRH (C.I. 73,386), Indigosol Violet 15R (C.I. 59,321), Indigosol Red Violet IRRL (C.I. 59,316), Indigosol Red IFBB (C.I. 67,001), Indanthrene Red Violet RRK (C.I. 67,895), Mikethren Brilliant Violet BBK (C.I. 63,355), etc. Further, cyan dyes generally used include azo dyes such as Direct Sky Blue 6B (C.I. 24,410), Direct Blue 2B (C.I. 22,610), Direct Brilliant Blue RW (C.I. 24,280), Sumilight Supra Blue G (C.I. 34,200), etc.; phthalocyanine compounds such as Sumilight Supra Turkish Blue G (C.I. 74,180), Mikethren Brilliant Blue 4G (C.I. 74,140), etc., and also azo dyes and vat dyeing dyes such as Indanthrene Turkish Blue 3GK (C.I. 67,915), Indanthrene Blue 5G (C.I. 69,845), Indanthrene Blue GCD (C.I. 69,810), Indigosol 04B (C.I. 73,066), Indigosol 04G (C.I. 73,046), Anthrasol Green IB (C.I. 59,826), etc.

Furthermore, the dyes described in U.S. Pat. Nos. 2,286,714, 2,286,837, 2,294,892, 2,294,893, 2,418,624, 2,420,630, 2,420,631, 2,612,448, 2,629,658, 2,705,708, 2,694,636, 3,002,964, 3,114,634 and 3,119,811 can be used in this invention.

The dyes incorporated in the photographic elements used in the process of this invention are bleachable dyes and a wide variety of dyes which are appropriate to the purpose of this invention can be used. The term "bleachable dye" as used in the description given herein includes dyes precursors, that is, compounds which color during the development or during other processing steps. The dyes used in this invention also include bleachable dyes which are diffusible but become non-diffusible upon dyeing a binder such as gelatin, bleachable dyes which are diffusible but become non-diffusible by using a suitable mordant, such as described in U.S. Pat. No. 2,882,156, and bleachable dyes which are non-diffusible in a silver halide emulsion.

The photographic element used in this invention may have a single silver halide emulsion layer or coating for obtaining a monochromatic dye image, which may be colored or a neutral gray, formed by a single dye or a mixture of dyes. Typical useful neutral dyes for such a photographic material are the azo dyes as described in British Pat. No. 999,996.

Also, the photographic element used in this invention may have a plurality of layers and contain a plurality of different bleachable dyes for forming natural or multicolor images. A particularly useful photographic element which can be employed in this invention has at least three silver halide emulsion layers which respectively contain a non-diffusible yellow dye, a non-diffusible magenta dye and a non-diffusible cyan dye and which have been sensitized, respectively, to blue light, green light and red light.

The silver halide emulsion layer used in this invention preferably contains a bleachable dye. However, if desired, the bleachable dye can be incorporated in an alkali-permeable layer adjacent the silver halide emulsion layer and this approach is sometimes preferred. With such a configuration, the speed of the color photographic material can be increased when the dye-containing layer is disposed under the silver halide emulsion layer. An example of such a configuration is a multilayer color photographic element having formed, in succession, on a support the following layers: a blue-sensitive silver halide-containing layer, a bleachable yellow dye-containing layer, a green-sensitive silver halide-containing layer, a bleachable magenta dye-containing layer, a red-sensitive silver halide-containing layer, and a bleachable cyan dye-containing layer.

In one embodiment of the present invention, the dyes may be incorporated in a processing bath, and the dyes used for the purpose are water-soluble and diffusible dyes. In this case, the gelatin in a photographic element is dyed by the diffusible dye and the dye thus becomes non-diffusible. Also, by using an appropriate mordant in the photographic element, the diffused dye can be rendered non-diffusible.

Appropriate mordants which can be used for this purpose are the polymers described in British Pat. No. 685,475, U.S. Pat. Nos. 2,675,316, 2,839,401, 2,882,156, 3,048,487, 3,184,309 and 3,445,231, West German Patent Application (OLS) No. 1,914,362 and Japanese Patent Application (OPI) Nos. 47624/75 (The term "OPI" as used herein refers to a "published unexamined Japanese patent application") and 71332/75.

The photographic material used in the present invention contains a silver salt which is capable of forming an imagewise distribution of silver. Suitale silver salts are silver halides such as silver chloride, silver bromide, silver iodide, silver chlorobromide, silver iodobromide, and silver chloroiodobromide and silver salts of organic acids such as silver behenate.

Furthermore, photographic materials of a non-silver salt type such as zinc oxide photographic materials may be also used as the photographic materials employed in the present invention. In this case, an imagewise distribution of silver is obtained by physically developing the photographic material using a silver salt after imagewise exposure. Moreover, the silver nuclei may be formed by physical development as described in Dutch Pat. No. 6,603,640, German Pat. No. 1,216,685 and U.S. Pat. No. 3,157,502.

The dye bleach bath used in the process of this invention is preferably an aqueous solution, although a water-miscible organic solvent (for example, methanol, ethanol, acetone, etc.) can be added to the dye bleach bath, if desired.

The dye bleach bath contains at least one stannous salt. More preferably, it contains further an organic phosphonic acid or an alkali metal salt thereof as already discussed. Moreover, if desired, the dye bleach bath may also contain a pH buffering agent such as a phosphate, a carbonate, etc.; a salt such as a sulfate, a perchlorate, a nitrate, etc.; an alkali such as sodium hydroxide, ammonium hydroxide, etc.; and an acid such as sulfuric acid, nitric acid, phosphoric acid, acetic acid and citric acid. Furthermore, the dye bleach bath may contain a bispyridinium compound.

The pH of the dye bleach solution is about 10 or more, preferably 11 or more, and more preferably in a range of 12 to 13.5. The amount of the stannous salt used in the solution is about $1 \times 10^{-3}$ to about 1 mol/liter, preferably about $1 \times 10^{-2}$ to 0.5 mol/liter, more preferably about 0.05 to 0.2 mol/liter. The amount of the organic phosphonic acid or salt thereof is about $5 \times 10^{-3}$ to about 1 mol/liter, preferably about $1 \times 10^{-2}$ to $5 \times 10^{-1}$ mol/liter. The amount of the bispyridinium added is about $5 \times 10^{-5}$ to about $2 \times 10^{-2}$ mol/liter, preferably about $1 \times 10^{-4}$ to $1 \times 10^{-2}$ mol/liter, more preferably about $2 \times 10^{-4}$ to $5 \times 10^{-3}$ mol/liter. While the bispyridinium can be added to the dye bleach solution if it is used immediately, as explained below, it is preferably incorporated in a fixing solution and carried into the dye bleach solution during processing.

The developer used for forming an image pattern of developed silver in a photographic element containing silver halide is a developer containing at least one developing agent such as an aminophenol (for example, 4-(N-methylamino)-phenol, N,N-diethyl-p-aminophenol, etc.); a 3-pyrazolidone (e.g., 1-phenyl-3-pyrazolidone, 4,4-dimethyl-1-phenyl-3-pyrazolidone, 4-methyl-4-hydroxymethyl-1-phenyl-3-pyrazolidone, 4,4-dihydroxymethyl-1-phenyl-3-pyrazolidone, etc.); a dihydroxybenzene (e.g., hydroquinone, methylhydroquinone, chlorohydroquinone, catechol, 4-phenylcatechol, etc.); ascorbic acid; and p-phenylenediamines.

The developer may further contain, if desired, the following additives.

For example, alkali agents and buffering agents such as sodium hydroxide, potassium hydroxide, sodium carbonate, potassium carbonate, sodium tertiary phosphate, potassium tertiary phosphate, potassium metaborate, and borax can be used individually or as a combination thereof. Also, for the purposes of imparting a buffering capability to the developer, for certain reasons of preparation of the developer, and further for increasing the ionic strength of the developer, various salts such as disodium hydrogen-phosphate, dipotassium hydrogenphosphate, potassium dihydrogenphosphate, sodium dihydrogenphosphate, sodium hydrogencarbonate, potassium hydrogencarbonate, boric acid, an alkali metal nitrate, an alkali metal sulfate, etc., may be used in the developer.

Furthermore, if desired, the developer used in this invention may contain a development accelerator. Examples of useful development accelerators are the various pyridinium compounds and other cationic compounds as described in U.S. Pat. Nos. 2,648,604 and 3,671,247 and Japanese Patent Publication No. 9503/69; cationic dyes such as phenosafranine; neutral salts such as thallium nitrate and potassium nitrate; polyethylene glycol and the derivatives thereof as described in Japanese Patent Publication No. 9504/69 and U.S. Pat. Nos. 2,533,990, 2,531,832, 2,950,970 and 2,577,127; nonionic compounds such as polythioethers; the organic solvents and organic amines as described in Japanese Patent Publication No. 9509/69 and Belgian Pat. No. 682,862; ethanolamine; ethylenediamine; diethanolamine; and also the development accelerators as described in L. F. A. Mason, *Photographic Processing Chemistry*, pp. 40–43, Focal Press, London (1966).

Other examples of useful development accelerators which can be employed in this invention are benzyl alcohol and phenylethyl alcohol as described in U.S. Pat. No. 2,515,147, and pyridine, ammonia, hydrazine and the amines as described in *Journal of the Society of Photographic Science and Technology of Japan*, Vol. 14, p. 74 (1952).

Moreover, sodium sulfite, potassium sulfite, potassium hydrogensulfite, sodium hydrogensulfite, etc., which are usually used as preservatives may be employed in the developer used in this invention.

Also, the developer used in this invention may further contain, if desired, an antifoggant. Examples of antifoggants include an alkali metal halide such as potassium bromide, sodium bromide, potassium iodide, etc., as well as organic antifoggants. Examples of organic antifoggants are nitrogen-containing heterocyclic compounds such as benzotriazole, 6-nitrobenzimidazole, 5-nitroisoindazole, 5-methylbenzotriazole, 5-nitrobenzotriazole, 5-chlorobenzotriazole, etc.; mercapto-substituted heterocyclic compounds such as 1-phenyl-5-mercaptotetrazole, 2-mercaptobenzimidazole, 2-mercaptobenzothiazole, etc.; and mercapto-substituted aromatic compounds such as thiosalicylic acid, etc. The amount of the antifoggant generally used is about 1 mg to about 5 g, preferably 5 mg to 1 g, per liter of the developer.

Still further, polyphosphoric acid compounds such as sodium hexametaphosphate, sodium tetrapolyphosphate, sodium tripolyphosphate, potassium hexametaphosphate, potassium tetrapolyphosphate, potassium tripolyphosphate, etc.; and aminopolycarboxylic acids such as phosphonocarboxylic acids, ethylenediaminetetraacetic acid, nitrilotriacetic acid, cyclohexanediaminetetraacetic acid, iminodiacetic acid, N-hydroxymethylethylenediaminetriacetic acid, diethylenetriaminepentaacetic acid, etc., may be also used as a water softener in the developer. The amount of the water softener depends upon the hardness of water used but is usually about 0.5 to about 1 g/liter.

Furthermore, a calcium or magnesium sequestering agent may be used in the photographic processing solution as described in detail in J. Willems, *Belgische Chemische Industrie*, Vol. 21, 325 (1956) and ibid., Vol. 23, 1105 (1958).

Photographic fixing solutions containing one or more silver halide solvents which are conventionally used can be used as a fixing solution in the present invention. Fixing agents well known in the art can be used as the silver halide solvent. Specific examples of suitable fixing agents are thiosulfates such as sodium thiosulfate, potassium thiosulfate, etc.; thiocyanates such as potassium thiocyanate, sodium thiocyanate, etc.; organic amines such as alkanolamine, etc.; and thioether compounds.

The fixing solution preferably contains the bispyridinium salt. In accordance with the invention the bispyridinium salt may be incorporated directly into the silver dye bleach bath if the bath is to be used immediately, but due to the instability of the bispyridinium salt in the silver dye bleach bath, the salt is preferably incorporated in a fixing solution employed before the dye bleach solution and carried into the dye bleach solution upon processing. The pH of the fixing solution is about 2.5 to about 11, preferably about 3 to about 9. The amount of the fixing agent is about 0.06 to 2.5 mol/liter, preferably about 0.6 to about 1.3 mol/liter. The amount of the bispyridinium added is about $5 \times 10^{-5}$ to about 0.1 mol/liter, preferably about $5 \times 10^{-5}$ to about $2 \times 10^{-2}$ mol/liter, more preferably about $2 \times 10^{-4}$ to about $5 \times 10^{-3}$ mol/liter.

Also, a monobath developer-fixer solution which is prepared by adding a silver halide solvent to a developer can be used without using a fixing solution. The fixing agents described above can be also used in the monobath developer-fixer solution. The monobath developer-fixer solution described in, for example, L. F. A. Mason, *Photographic Processing Chemistry*, pp. 156–160, Focal Press, London (1966) can be used.

The color photographic element used in the present invention may also contain non-photosensitive photographic layers (for example, an antihalation layer, an interlayer for preventing color mixing, a yellow filter layer, a protective layer, etc.). The position on the support of the red-sensitive layer, the green-sensitive layer and the blue-sensitive layer is not particularly limited.

Each dye may be present in a layer containing silver halide or may be present in a photographic layer adjacent a silver halide emulsion layer.

The color photographic element processed in the process of this invention may contain silver bromide, silver chloride, silver chlorobromide, silver iodobromide or silver iodochlorobromide as the silver halide in the photographic emulsion layer or layers. When the color photographic element has two or more photographic emulsion layers, a combination of two or more of the silver halides described above may be employed.

The silver halide photographic emulsion may be prepared using the processes described in P. Grafkides, *Chimie Photographique*, Paul Montel, Paris (1967) and further the silver halide emulsion may also be prepared using any one of an ammonia method, a neutral method, an acid method, a single jet method, a reverse mixing method, a double jet method, and a controlled double jet method.

The crystal form of the silver halide grains may be that of a cubic system, an octahedral system, or a mixed crystal system thereof. The silver halide grains used in this invention may be the type having a uniform crystal structure throughout the grain, may be the type having a layered structure where the surface of the grain is different from the interior of the grain, or may be the so-called conversion type as described in British Pat. No. 635,841 and U.S. Pat. No. 3,622,318. Furthermore, the silver halide grains used in this invention may be the type forming a latent image mainly on the surface of the grain or may be the type forming a latent image in the interior of the grain.

The silver halide emulsion used in this invention may be chemically sensitized using known methods. For chemical sensitization, the sulfur compounds as described in U.S. Pat. No. 1,574,944, the gold compounds as described in U.S. Pat. No. 2,399,083, the compounds of noble metals such as platinum, palladium, iridium, rhodium, ruthenium, etc., as described in U.S. Pat. Nos. 2,448,060 and 2,598,079 and British Pat. No. 618,061, and reducing agents such as stannous salts and amines may be used.

In the photographic layers of the photographic light-sensitive materials processed by the process of this invention, gelatin is usually used as the hydrophilic colloid but hydrophilic colloids other than gelatin may be used. For example, gelatin derivatives; graft polymers of gelatin with other polymers; cellulose derivatives such as hydroxyethyl cellulose, carboxymethyl cellulose, cellulose sulfate, etc.; saccharide derivatives such as sodium alginate, starch derivatives, etc.; and various other synthetic hydrophilic polymers such as polyvinyl alcohol, polyvinyl alcohol partial acetal, poly-N-vinyl pyrrolidone, polyacrylic acid, polymethacrylic acid, polyacrylamide, polyvinyl imidazole, polyvinyl pyrazole, etc., can be used.

In addition, lime treated gelatin, acid treated gelatin, a hydrolyzed product of gelatin, and an enzyme treated gelatin can be used as the gelatin.

Gelatin derivatives which can be used are those which are obtained by reacting gelatin with various kinds of compounds, for example, an acid halide, an acid anhydride, an isocyanate, a bromoacetic acid, an alkanesultone, a vinylsulfonamide, a maleinimide compound, a polyalkylene oxide, and an epoxy compound. Specific examples of gelatin derivatives are described in U.S. Pat. Nos. 2,614,928, 3,132,945, 3,186,846 and 3,312,553, British Pat. Nos. 861,414, 1,033,189 and 1,005,784, Japanese Patent Publication No. 26845/67, etc.

Gelatin graft polymers which can be used are those which are obtained by grafting a polymer or copolymer of a vinyl monomer such as acrylic acid, methacrylic acid, or an ester or an amide derivative thereof, acrylonitrile, styrene, etc., to gelatin. Particularly preferred polymers are those compatible with gelatin to some extent, e.g., polymers of acrylic acid, methacrylic acid, acrylamide, methacrylamide, and hydroxyalkyl methacrylates, etc. Examples of these compounds are described in U.S. Pat. Nos. 2,763,625, 2,831,767 and 2,956,884, etc.

Typical synthetic hydrophilic high molecular weight materials are described, for example, in German Patent Application (OLS) No. 2,312,708, U.S. Pat. Nos. 3,620,751 and 3,879,205, Japanese Patent Publication No. 7561/68, etc.

The light-sensitive materials used in this invention may further contain the hardening agents as described in U.S. Pat. No. 3,325,287; plasticizers such as the compounds as described in U.S. Pat. No. 3,775,128, and glycerol; alkylbenzene sulfonic acid, alkylene oxide condensation products, the compounds as described in U.S. Pat. Nos. 2,739,891 and 3,415,649, and other surface active agents; and other additives for improving the photographic properties, image characteristics, and physical properties of the light-sensitive materials.

The photographic element processed by the process of this invention may contain an ultraviolet absorbent in a hydrophilic colloid layer. Examples of such ultraviolet absorbents are aryl-substituted benzotriazole compounds as described in, for example, U.S. Pat. No. 3,533,794; 4-thiazolidone compounds as described in, for example, U.S. Pat. Nos. 3,314,794 and 3,352,681; benzophenone compounds as described in, for example, Japanese Patent Application (OPI) No. 2784/71; cinnamic acid esters as described in U.S. Pat. Nos. 3,705,805 and 3,707,375; and benzoxazole compounds as described in, for example, U.S. Pat. No. 3,499,762.

Moreover, the hydrophilic colloid layers of the light-sensitive materials processed by the process of this invention may further contain stilbene series fluorescent brightening agents, triazine series brightening agents, oxazole series brightening agents, or cumarin series brightening agents. They may be water-soluble or water-insoluble and in the latter case they may be used as dispersions thereof. Suitable examples of these fluorescent brightening agents are described in U.S. Pat. Nos. 2,632,701, 3,269,840 and 3,359,102 and British Pat. No. 1,319,763.

For obtaining a photographic image, the light-sensitive material is first imagewise exposed in an ordinary manner. That is, various light sources such as natural light (sunlight), a tungsten lamp, a fluorescent lamp, a mercury lamp, a xenon arc lamp, a carbon arc lamp, a xenon flash lamp, a cathode ray tube flying spot, etc., may be employed for the exposure. The exposure time usually ranges from about 1/1,000 second to 1 second as generally used for camera exposure but a shorter exposure time, for example, about $1/10^4$ to about $1/10^6$ second using a xenon flash lamp or a cathode ray tube flying spot and also an exposure longer than 1 second can be employed in this invention. If desired, the spectral composition of the light used for exposure can be controlled by a color filter. Furthermore, laser light may be used for the exposure. Moreover, the exposure may be performed using the light emitted from a phosphor excited by an electron beam, X-rays, gamma rays, alpha rays, etc.

The process of this invention is superior to conventional processes. Some of the advantages of the process of this invention are set forth below.

(1) Color images having excellent light fastness, heat resistance, and moisture resistance as compared with those obtained by conventional color development processing are obtained.

(2) The amount of silver or silver salt in the color photographic materials can be greatly reduced as compared with that required for conventional color development processing, the silver dye bleach method, and the color intensification method.

(3) Since the amount of silver or silver salt and the amount of polymers such as gelatin in the color photographic materials can be reduced, the thickness of the emulsion layers can be reduced effectively, which results in increasing the sharpness of the images obtained.

(4) Chemicals such as p-phenylenediamine derivatives which are hazardous, usually used in conventional color development processing, and a strongly acidic processing solution having a strong corrosive activity, usually used in a conventional silver dye bleach process, do not need to be used in this invention.

(5) As compared with a color intensification process using a cobalt (III) complex and hydrogen peroxide, the process of this invention is simple in terms of the processing steps involved.

The invention is further described more specifically by reference to the following examples but the invention is not to be construed as being limited to the embodiments illustrated in these examples.

EXAMPLE 1

A photographic element was prepared by coating on a cellulose triacetate support having a subbing layer thereon a silver iodobromide emulsion (silver iodide: 4 mol%; mean grain size: 0.7 micron) containing a cyan dye (coated amount: 806 mg/m$^2$) having the structure shown below:

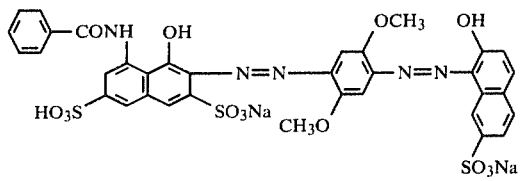

at a coated amount of silver of 50 mg/m$^2$ and then coating thereon a gelatin protective layer at a coated amount of gelatin of 1,000 mg/m$^2$.

The photographic element was exposed through an optical wedge using an actinometer to a tungsten lamp of a color temperature of 2,854° K. at a maximum of 1,000 CMS and then processed in one of the following two Processes A and B.

| | Process A (process of this invention) | |
|---|---|---|
| Processing | Temperature (°C.) | Time |
| Development | 25 | 2 min |
| Fix | " | 1 min |
| Wash | " | 30 sec |
| Dye Bleach | 40 | 30 sec to 2 min |
| Wash | 25 | 1 min |

-continued

| | | |
|---|---|---|
| Blix | 40 | 2 min |
| Wash | 25 | 2 min |

The compositions of the processing solutions used in the above processing were as follows:

Developer

| | |
|---|---|
| Disodium Ethylenediaminetetraacetate | 1 g |
| Sodium Sulfite | 60 g |
| Hydroquinone | 10 g |
| Sodium Hydroxide | 5 g |
| Diethylene Glycol | 20 ml |
| 1-Phenyl-3-pyrazolidone | 0.4 g |
| Sodium Carbonate | 20 g |
| Potassium Bromide | 9 g |
| Benzotriazole | 0.1 g |
| Water to make | 1 l |

Fixing Solution

| | |
|---|---|
| Sodium Thiosulfate (crystalline) | 240 g |
| Sodium Sulfite | 15 g |
| Glacial Acetic Acid | 13.3 g |
| Boric Acid | 7.5 g |
| Potassium Alum | 15 g |
| Compound 3 | 1.9 g |
| Water to make | 1 l |

Dye Bleach Solution

| | |
|---|---|
| Stannous Chloride (dihydrate) | 10 g |
| Hydroxyethylidene-1,1-diphosphonic Acid (60%) | 30 ml |
| Sodium Hydroxide (10%) | 300 ml |
| Water to make | 1 l |

Blix Solution

| | |
|---|---|
| Ammonium Thiosulfate | 150 ml |
| Sodium Sulfite | 5 g |
| Sodium [Iron (III)-ethylenediamine-tetraacetic acid complex salt] | 40 g |
| Disodium Ethylenediaminetetraacetate | 4 g |
| Water to make | 1 l |

Process B (silver dye bleach process for comparison)

| Processing | Temperature (°C.) | Time |
|---|---|---|
| Development | 25 | 4 min |
| Wash | " | 2 min |
| Dye Bleach | 40 | 7–13 min |
| Wash | 25 | 1 min |
| Blix | " | 3 min |
| Wash | " | 3 min |

The compositions of the processing solutions used were as follows:

Developer
Same as the developer composition of Process A.

Dye Bleach Solution

| | |
|---|---|
| Hydrochloric Acid (conc.) | 100 ml |
| Phenazine | 18 mg |
| Thiourea | 100 g |
| Water to make | 1 l |

Blix Solution
Same as blix solution composition of Process A.
The results obtained are shown in Table 1 below.

TABLE 1

| Process | Dye Bleaching time (min) | Maximum Cyan Density | Minimum Cyan Density | Gamma Value | Sensitivity* |
|---|---|---|---|---|---|
| Process A (invention) | 0.5 | 2.02 | 0.08 | 1.5 | 1.0 |
| | 1 | 2.01 | 0.06 | 2.0 | 1.3 |
| | 2 | 2.02 | 0.05 | 2.4 | 1.5 |
| Process B (comparison) | 7 | 2.00 | 1.56 | 0.24 | — |
| | 10 | 2.01 | 1.55 | 0.25 | — |
| | 13 | 2.00 | 1.55 | 0.25 | — |

*Relative sensitivity when the sensitivity of the photographic element processed for 0.5 minute in Process A was designated as 1.00. In Process B, the sensitivity value could not be determined since the minimum density was too high.

The conventional silver dye bleach process (Process B) required one equivalent of silver for bleaching the dye and, hence, when the process was applied to a low-silver light-sensitive material (mol ratio of silver to dye: 1:2) used in this example, insufficient bleaching resulted. This is clearly indicated by a small difference between the maximum cyan density and the minimum cyan density which resulted in poor image discrimination.

On the other hand, in Process A of this invention, the silver acted catalytically and, hence, the bleaching was performed sufficiently and cyan positive images having a low minimum density images having superb image discrimination were obtained. Also, by prolonging the time for the dye bleaching in the process of this invention, the sensitivity could be increased.

EXAMPLE 2

A photographic element was prepared using the same procedure as described in Example 1 except that a magenta dye (coated amount: 854 mg/m²) having the structure shown below:

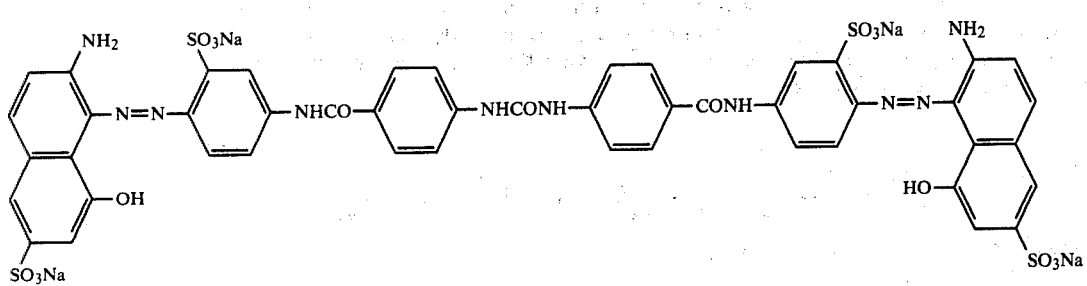

was used in place of the cyan dye and except that the coated amount of silver was 100 mg/m². The photographic element was exposed under the same conditions as in Example 1 and processed using Process A as described in Example 1 except that the dye bleach processing time was 3 minutes and the following fixing solution and dye bleach solution were used.

Fixing Solution

| | |
|---|---|
| Sodium Thiosulfate | 240 g |
| Sodium Sulfite | 15 g |

|  | -continued |
| --- | --- |
| Glacial Acetic Acid | 13.3 g |
| Boric Acid | 7.5 g |
| Potassium Alum | 15 g |
| Water to make | 1 l |

| Dye Bleach Solution | C | D* | E | F | G |
| --- | --- | --- | --- | --- | --- |
| Stannous Chloride (dihydrate) | 10 g | 10 g | 10 g | 10 g | 10 g |
| Hydroxyethylidene-1,1-diphosphoric Acid (60%) | — | — | 30 ml | — | 30 ml |
| Triethanolamine | — | 10 ml | — | — | — |
| Anthraquinone | — | 2.5 mg | — | — | — |
| Compound 3 | — | — | — | 400 mg | 400 mg |
| Sodium Hydroxide (30%) | 300 ml | 300 ml | 300 ml | 300 ml | 300 ml |
| Water to make | 1 l | 1 l | 1 l | 1 l | 1 l |
|  | Comparison | Comparison | Comparison | Invention | Invention |

*System described in U.S. Pat. No. 2,184,022.

The results obtained are shown in Table 2 below.

TABLE 2

| Dye Bleach Solution | Minimum Magenta Density | Maximum Magenta Density | Gamma Value |
| --- | --- | --- | --- |
| C | 2.40 | 2.50 | <0.1 |
| D | 1.90 | 2.45 | 0.7 |
| E | 2.40 | 2.51 | <0.1 |
| F | 0.11 | 2.50 | 2.7 |
| G | 0.08 | 2.50 | 2.8 |

As is clearly understood from the data shown above the images formed could not be discriminated in C where only stannous chloride was present and in E where stannous chloride alone was present in combination with the phosphoric acid. Also, in D where anthraquinone was used following the teaching of U.S. Pat. No. 2,184,022, image discrimination was poor. On the other hand, F which is the system of the present invention provided excellent image discrimination. The system G in which the chelating phosphoric acid was further incorporated provided more excellent image discrimination. In addition, it is also understood from the gamma value that the systems F and G give sharper images as compared to the systems C, D and E.

EXAMPLE 3

A photosensitive element was prepared using the same procedure as described in Example 1 except that a yellow dye (coated amount: 1,580 mg/m$^2$) having the structure shown below:

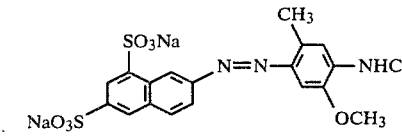

was used in place of the cyan dye and the coated amount of silver was 100 mg/m$^2$. The photographic element was exposed through an optical wedge using an actinometer to light from a tungsten lamp of a color temperature of 2,854° K. at a maximum of 10,000 CMS and then processed using Process A as described in Example 1.

Using a dye bleach processing time of 2 minutes, yellow positive images having a maximum yellow density of 2.0, a minimum yellow density of 0.03 and a gamma value of 1.8 were obtained. Good image discrimination was obtained.

EXAMPLE 4

A photographic element was prepared as described in Example 1, was exposed under the same conditions as in Example 1, and was processed using processing solutions having the same compositions described in Process A of Example 1 except that the following fixing solution and dye bleach solution were used.

| Fixing Solution | |
| --- | --- |
| Sodium Thiosulfate | 240 g |
| Sodium Sulfite | 15 g |
| Glacial Acetic Acid | 13.3 g |
| Boric Acid | 7.5 g |
| Potassium Alum | 15 g |
| Water to make | 1 l |
| Dye Bleach Solution | |
| Sodium Gluconate | 50 g |
| Stannous Chloride (dihydrate) | 10 g |
| Compound 3 | 370 mg |
| Water to make | 1 l |

Using a 10% aqueous sodium hydroxide solution to adjust pH of 13.0.

Using a dye bleach processing time of 2 minutes, cyan positive images have a maximum cyan density of 2.01, a minimum cyan density of 0.05 and a gamma value of 2.35 were obtained. The results indicate that the similar photographic properties are obtained to those in Process A of Example 1 when Compound 17 is added to the dye bleach solution as a catalyst. Good image discrimination was obtained.

EXAMPLE 5

A photographic element (silver coverage: 200 mg/m$^2$) was prepared by coating a silver iodobromide emulsion (silver iodide: 4 mol%; mean grain size: 0.7 micron) containing a cyan dye (806 mg/m$^2$) having the same structure as in Example 1 in the same manner as described in Example 1. The photographic element was exposed under the same conditions as in Example 1 and processed as follows:

| | Temperature | Time |
| --- | --- | --- |

-continued

| Processing Step | (°C.) | (min) |
| --- | --- | --- |
| Development | 25 | 2 |
| Wash | " | 1 |
| Dye Bleach | 50 | 2 |
| Wash | 25 | 1 |
| Blix | " | 2 |
| Wash | " | 2 |

The compositions of the processing solutions used in the above processing were as follows:

Developer (monobath development-fix solution)

| | |
| --- | --- |
| 1-Phenyl-3-pyrazolidone | 1.0 g |
| Sodium Sulfite | 30 g |
| Hydroquinone | 10 g |
| Sodium Carbonate (anhydrous) | 20 g |
| Sodium Hydroxide | 5 g |
| Sodium Thiosulfate (crystalline) | 60 g |
| Water to make | 1 l |

Dye Bleach Solution

| | |
| --- | --- |
| Stannous Chloride (dihydrate) | 10 g |
| Hydroxyethylidene-1,1-diphosphoric Acid (60%) | 30 ml |
| Compound 2 | 1 g |
| Water to make | 1 l |

Blix Solution

Same as the blix solution in Process A as described in Example 1.

Cyan positive images having a maximum cyan density of 2.0, a minimum cyan density of 0.02 and a gamma value of 2.4 were obtained. Good image discrimination was obtained.

While the invention has been described in detail and with reference to specific embodiments thereof, it will be apparent to one skilled in the art that various changes and modifications can be made therein without departing from the spirit and scope thereof.

What is claimed is:

1. A process for forming color images which comprises processing a photographic light-sensitive element containing imagewise distributed silver therein with an aqueous alkaline solution having a pH of about 10 or more containing a stannous ion and in the presence of a dye and a bispyridinium compound represented by the following general formula (I):

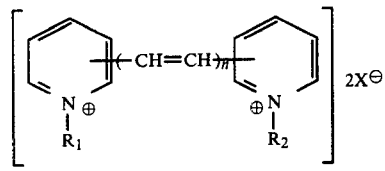

wherein $R_1$ and $R_2$ each represents a lower aliphatic hydrocarbon group or $R_1$ and $R_2$ are bonded to each other to form a ring; n represents 0 or 1; and $X^-$ represents an anion; to bleach the dye in an imagewise manner.

2. The process of claim 1, wherein the photographic light-sensitive element is processed with an alkaline solution containing a stannous ion and an organic phosphonic acid.

3. The process of claim 1, wherein the bispyridinium compound is a compound represented by the following general formula (Ia) or (Ib):

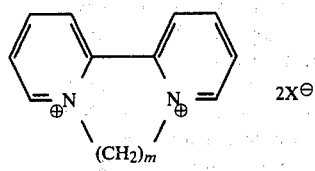

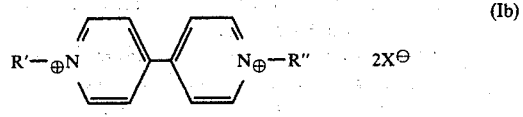

wherein m represents an integer of 2 to 4; R' and R" each represents an alkyl group having 1 to 3 carbon atoms; and $X^-$ represents an anion.

4. The process of claim 1, wherein the organic phosphonic acid or the salt thereof is a compound represented by the following formula (III):

$$R_4R_5C(PO_3M_2)_2 \qquad (III)$$

wherein $R_4$ represents a hydrogen atom, an alkyl group having 1 to 4 carbon atoms, an aralkyl group, an alicyclic group, $-CHR_6-PO_3M_2$ (wherein $R_6$ represents a hydrogen atom, a hydroxy group or an alkyl group) or $-PO_3M_2$; $R_5$ represents a hydrogen atom, a hydroxy group, an alkyl group, a substituted alkyl group or $-PO_3M_2$; M represents a hydrogen atom or a cation capable of providing water solubility.

5. The process of claim 1, wherein said organic phosphonic acid or salt thereof is represented by the following formula (IV):

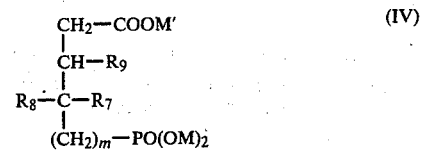

wherein $R_7$ represents $-COOM'$ or $-PO(OM)_2$; $R_8$ represents a hydrogen atom, an alkyl group having 1 to 4 carbon atoms, $-(CH_2)_nCOOM'$ or a phenyl group; $R_9$ represents a hydrogen atom or $-COOM'$; M and M' each represents a hydrogen atom, an alkali metal atom or an ammonium group; m is 0 or 1; and n represents 1 to 4.

6. The process of claim 2, wherein said organic phosphonic acid or salt thereof is represented by the formula (II):

$$R_3N(CH_2PO_3M_2)_2 \qquad (II)$$

wherein M represents a hydrogen atom or a cation capable of rendering the compound soluble and $R_3$ represents an alkyl group containing 1 to 4 carbon atoms, an aryl group, an aralkyl group, an alicyclic group, or a heterocyclic group.

7. The process of claim 1, wherein said dye is a reducibly bleachable dye.

8. The process of claim 7, wherein said dye is an azo dye.

9. The process of claim 1, wherein said dye is present in said light-sensitive element in a silver halide emulsion layer or a layer adjacent a silver halide emulsion layer.

10. The process of claim 1, wherein the aqueous alkaline solution has a pH of about 12 to 13.5.

11. The process of claim 1, wherein said aqueous alkaline solution contains a stannous salt selected from the group consisting of $SnCl_2$, $SnSO_4$, $Sn(NO_3)_2$, $Sn(CH_3COO)_2$ and $SnC_2O_4$.

12. The process of claim 1, wherein said aqueous alkaline solution contains a stannous salt in an amount of about $1 \times 10^{-3}$ to about 1 mol/liter.

13. The process of claim 2, wherein said organic phosphonic acid is present in said solution in an amount of $5 \times 10^{-3}$ to about 1 mol/liter.

14. The process of claim 1, wherein said bispyridinium compound is present in a fixing solution.

15. The process of claim 1, wherein said bispyridinium compound is present in said solution containing said stannous ion.

16. The process of claim 14, wherein said bispyridinium compound is present in said fixing solution in an amount of about $5 \times 10^{-5}$ to 0.1 mol/liter.

17. The process of claim 1, wherein positive color images are formed.

18. A process of forming color positive images which comprises developing an imagewise exposed photographic element comprising a support having thereon at least one layer containing a silver halide emulsion and a dye to form an image pattern of developed silver, fixing the photographic element with a fixing solution containing a bispyridinium compound represented by the following general formula (I):

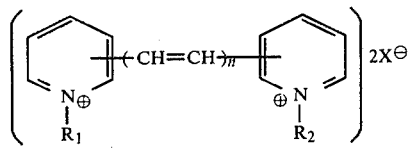

wherein $R_1$ and $R_2$ each represents a lower aliphatic hydrocarbon group or $R_1$ and $R_2$ are bonded to each other to form a ring; n represents 0 or 1; and $X^-$ represents an anion, and a thiosulfate; processing the fixed photographic element with an alkaline aqueous solution having a pH of 10 or more containing a stannous salt to bleach the dye in an imagewise manner and then blixing the photographic element to remove the development silver.

19. The process of claim 18, wherein the photographic light-sensitive element is processed with an alkaline aqueous solution containing a stannous salt and an organic phosphonic acid or salt thereof.

20. The process of claim 18, wherein the bispyridinium compound is a compound represented by the following formula (Ia) or (Ib):

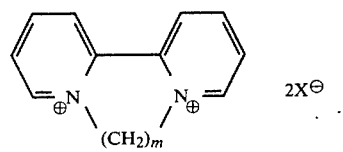

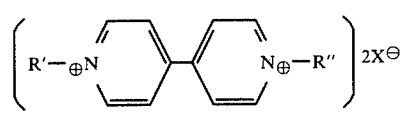

wherein m represents an integer of 2 to 4; R' and R" each represents an alkyl group having 1 to 3 carbon atoms; and $X^\ominus$ represents an anion.

21. The process of claim 18, wherein the aqueous alkaline solution has a pH of 12 to 13.5.

22. The process of claim 18, wherein said dye is a reducibly bleachable dye.

23. The process of claim 22, wherein said dye is an azo dye.

24. The process of claim 18, wherein said stannous salt is selected from the group consisting of $SnCl_2$, $SnSO_4$, $Sn(NO_3)_2$, $Sn(CH_3COO)_2$ and $SnC_2O_4$.

25. The process of claim 18, wherein said stannous salt is present in an amount of about $1 \times 10^{-3}$ to 1 mol/liter.

26. The process of claim 19, wherein said phosphonic acid is present in an amount of about $5 \times 10^{-3}$ to 1 mol/liter.

27. The process of claim 18, wherein said bispyridinium compound is present in said fixing solution in an amount of about $5 \times 10^{-5}$ to $2 \times 10^{-2}$ mol/liter.

28. The process of claim 18, wherein said dye is present in a layer adjacent said silver halide emulsion layer.

29. The process of claim 18, wherein said photographic element comprises a support having thereon at least one blue-sensitive silver halide emulsion layer, a bleachable yellow dye-containing layer, a green-sensitive silver halide emulsion layer, a bleachable magenta dye-containing layer, a red-sensitive silver halide emulsion layer, and a bleachable cyan dye-containing layer.

30. The process of claim 18, wherein the organic phosphonic acid is 2-hydroxyethane-1,1-diphosphonic acid, 1-hydroxyethane-1,1-diphosphonic acid, ethane-1,1,1-triphosphonic acid, 1-hydroxyethane-1,1,2-triphosphonic acid or 2-phosphonobutane-1,2,4-tricarboxylic acid.

31. The process of claim 18, wherein the organic phosphonic acid is hydroxyethane-1,1-diphosphonic acid and the bispyridinium salt is a compound of the formula:

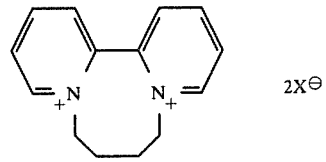

wherein $X^\ominus$ represents an anion.

32. The process of claim 1 wherein said photographic light-sensitive element contains silver in an amount substantially less than the amount stoichiometrically required to bleach said dye.

33. The process of claim 18 wherein said photographic light-sensitive element contains silver in an amount substantially less than the amount stoichiometrically required to bleach said dye.

34. The process of claim 1 wherein said photographic material contains less than about 3 g/m² silver.

35. The process of claim 18 wherein said photographic material contains less than about 3 g/m² silver.

36. The process of claim 1 wherein said photographic material contains less than about 2 g/m² silver.

37. The process of claim 18 wherein said photographic material contains less than about 2 g/m² silver.

38. The process of claim 1 wherein said photographic material contains silver in a catalytic amount substantially less than the amount stoichiometrically required to bleach said dye.

39. The process of claim 18 wherein said photographic material contains silver in a catalytic amount substantially less than the amount stoichiometrically required to bleach said dye.

* * * * *